United States Patent [19]

Janacek

[11] Patent Number: 5,667,493

[45] Date of Patent: Sep. 16, 1997

[54] DILATION CATHETER

[76] Inventor: Jaroslav Janacek, 32350 Thompson Rd., Winchester, Calif. 92596

[21] Appl. No.: 366,968

[22] Filed: Dec. 30, 1994

[51] Int. Cl.$^6$ ............................................. A61M 29/00
[52] U.S. Cl. ................................. 604/96; 606/194
[58] Field of Search ................. 604/96, 102, 103, 604/104, 282; 606/194

[56] References Cited

U.S. PATENT DOCUMENTS

| 4,195,637 | 4/1980 | Grüntzig et al. | 128/348 |
|---|---|---|---|
| 4,323,071 | 4/1982 | Simpson et al. | 128/343 |
| 4,762,129 | 8/1988 | Bonzel | 128/344 |
| 4,763,654 | 8/1988 | Jang | 128/344 |
| 4,909,252 | 3/1990 | Goldberger | 604/96 X |
| 4,983,167 | 1/1991 | Sohota | 606/194 |
| 5,061,273 | 10/1991 | Yock | 606/194 |
| 5,071,406 | 12/1991 | Jang | 604/96 |
| 5,217,482 | 6/1993 | Keith | 604/282 X |
| 5,304,132 | 4/1994 | Jang | 604/96 |
| 5,304,134 | 4/1994 | Kraus et al. | 604/96 |
| 5,330,528 | 7/1994 | Lazim | 606/194 X |
| 5,382,234 | 1/1995 | Cornelius et al. | 604/96 |
| 5,413,557 | 5/1995 | Solar | 604/96 |

*Primary Examiner*—Robert A. Hafer
*Assistant Examiner*—Perry E. Van Over
*Attorney, Agent, or Firm*—Watts, Hoffmann, Fisher & Heinke Co., L.P.A.

[57] ABSTRACT

A dilation catheter for use in performing angioplasty procedures. The catheter includes a relatively long catheter shaft which has two lumens. A relatively short guidewire receiving tube is thermally bonded to the distal end of the shaft, with its lumen approximately aligned with one of the lumens of the catheter shaft and a stiffening wire positioned therein. A dilation balloon, preformed with a shape that enables it to be used in an offset configuration, is thermally bonded to the distal and proximal ends of the tube, with its lumen aligned with the remaining lumen of the catheter shaft. The balloon and tube together define channels for the perfusion of blood past the balloon, which channels remain open even when the balloon bears against the tube during the inflation thereof.

19 Claims, 2 Drawing Sheets

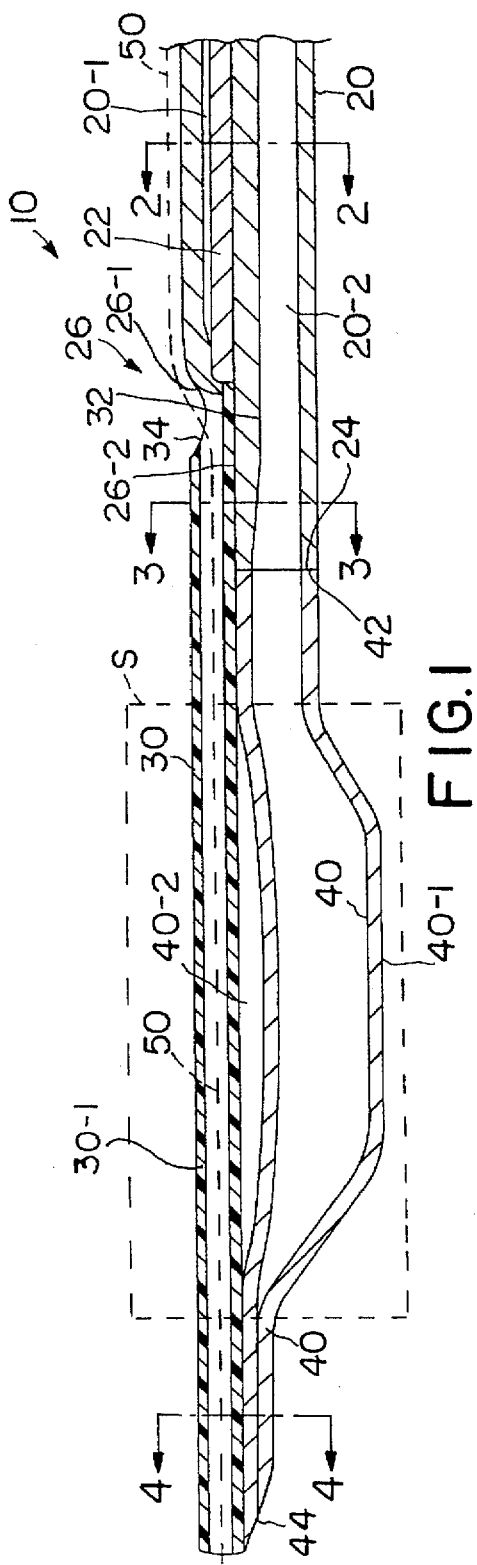
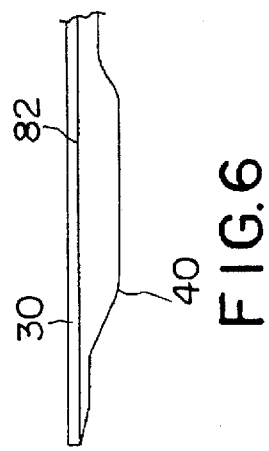
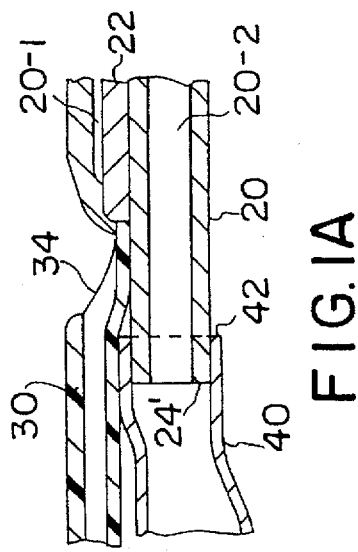
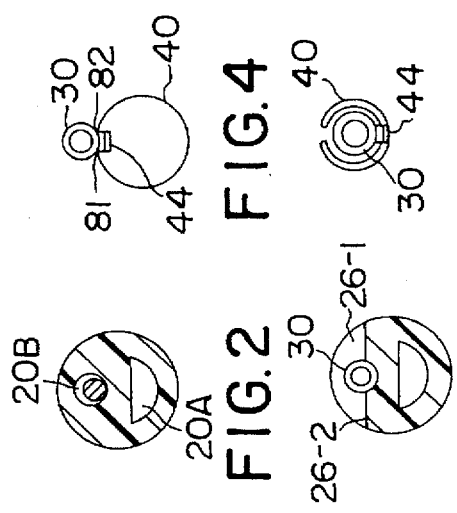

DILATION CATHETER

BACKGROUND OF THE INVENTION

The present invention relates to dilation catheters, and is directed more particularly to a dilation catheter which allows blood to flow thereby while it is being used to perform an angioplasty procedure.

The use of angioplasty to treat patients having stenoses, i.e., regions of constricted blood flow, in coronary arteries has become a widely accepted alternative to more invasive treatments. With this procedure the balloon of a dilation catheter is maneuvered into position across a stenoses, inflated to increase the size of the blood flow passage therethrough, and then deflated and withdrawn. In many cases this procedure has been found to produce a lasting increase in the rate of blood flow through the region of the stenoses thereby eliminating the need for coronary bypass surgery.

In many cases the angioplasty procedure must be performed on a succession of stenoses having different locations and sizes, necessitating the use of dilation catheters having different balloon sizes. In other cases it has been found that the proper treatment of a stenoses requires the application thereto of a succession of dilation balloons of progressively increasing size. Because the insertion of a dilation catheter into the body of a patient and the subsequent maneuvering thereof unavoidably presents some risk of injuring the walls of the patient's blood vessels, dilation catheters are used in conjunction with a guiding catheter which remains inside the patient throughout the procedure and which serves to protect the blood vessels from abrasion as successive dilation catheters are inserted and withdrawn.

Dilation catheters are also used in conjunction with a guidewire which, like the guiding catheter, remains within the patient when the dilation catheter is removed and replaced. This guidewire not only serves as a track or guide for the dilation catheter while it is inside of the guiding catheter, it also facilitates the final positioning of the balloon at a stenosis after the dilation catheter emerges from the end of the guiding catheter. Dilation catheters which may be exchanged without the removal and reinsertion of the guidewire are said to have a "rapid exchange capability". Examples of dilation catheters having such a rapid exchange capability are shown and described in U.S. Pat. Nos. 4,762,129 (Bonzel) and 5,061,273 (Yock).

In most cases the full benefit of the angioplasty procedure will not be realized if the dilation balloon is deflated immediately after being inflated. This is because it takes time for the material making up the stenoses to reconfigure itself and become consolidated into a mass that will not readily return to its original flow constricting shape. As a result, the balloon may have to be maintained in its inflated state for many seconds. This can result in a serious risk to the patient because, unless special provision is made for the perfusion of blood thereby, an inflated dilation balloon will stop the flow of blood through the vessel in which it is located. Dilation catheters which make provision for the perfusion of blood are said to have a "perfusion capability". Examples of dilation catheters having such a perfusion capability are shown and described in U.S. Pat. Nos. 4,763,654 (Jang) and 4,983,167 (Sahota).

The dilation balloons of dilation catheters are ordinarily of one of two types. A first of these types includes balloons which are distributed more or less symmetrically with respect to the associated guidewires. Examples of dilation catheters which include balloons of this type and which have a rapid exchange capability include the previously cited Bonzel and Yock patents. Examples of dilation catheters which include balloons of this type, but which do not have a rapid exchange capability, are described in U.S. Pat. Nos. 4,323,071 (Simpson et.al.) and 4,195,637 (Gruntzig et.al.). Dilation catheters having balloons of this type have the advantage that they act on a stenosis uniformly in all directions, but have the disadvantage that they are unable to present the stenosis with a surface that is relatively stiff, i.e., unyielding. Such a surface can be beneficial in the case of stenoses that are relatively hard and need to be, in effect, "cracked" open.

A second of these types includes balloons which are offset to one side of the associated guidewire. Examples of dilation catheters which include one or more balloons of this type are described in U.S. Pat. Nos. 5,071,406 (Jang) and 5,304,132 (Jang), neither catheter having either a rapid exchange capability or a perfusion capability. One advantage of dilation catheters having balloons of this type is that they are able to present at least part of a stenosis with a relatively stiff surface. Another advantage is that their lack of symmetry enables them to be oriented for use in treating stenoses that are distributed unsymmetrically within a blood vessel.

In view of the foregoing it will be seen that, prior to the present invention, there has not been available a dilation catheter which has both a rapid exchange capability and a perfusion capability, and yet which has all of the advantages of dilation catheters that include offset balloons.

SUMMARY OF THE INVENTION

In accordance with the present invention there is provided an improved dilation catheter which utilizes an offset dilation balloon and yet which has both a rapid exchange capability and a perfusion capability.

Generally speaking, the present invention comprises a dilation catheter including a catheter shaft, a guidewire receiving tube which has a length that is small in relation to the length of the catheter shaft and which is secured in proximity to the distal end of the catheter shaft, and a balloon which is offset to one side of the guidewire receiving tube and which is secured to that tube only at the proximal and distal end sections thereof. In use, a guidewire may be easily inserted into or removed from the guidewire receiving tube via a proximal exit port. This ease of insertion and removal, together with the distal positioning of the tube, endows the catheter with a rapid exchange capability. The offset positioning of the balloon, together with the difference in size between the balloon and the guidewire receiving tube, causes a longitudinal channel or groove to appear along the boundary therebetween. This channel, which allows blood to flow past the balloon when the latter is in its inflated state, endows the catheter with a perfusion capability. Thus, the dilation catheter of the invention has both a rapid exchange capability and a perfusion capability.

In the preferred embodiment, the catheter shaft is provided with two lumens. A first of these lumens is used as an inflation lumen to conduct a flow of a suitable inflating fluid to the balloon. The second lumen is used to carry a stiffening wire that terminates in proximity to the proximal exit port of the guidewire receiving tube. This stiffening wire endows the catheter with a measure of longitudinal stiffness that allows it to better maintain its shape as it is being pushed through the guiding catheter, and the torsional stiffness that allows it to be rotated once it has reached its final position. Terminating this stiffening wire in proximity to the exit port of the guidewire is particularly advantageous, since it allows the guidewire to take over the stiffening function of the stiffening wire at approximately the point where the stiffening wire ends. As a result, there is approximated a condition in which the catheter has the advantages associated with the presence of a continuous full length stiffening wire without the lack of rapid exchange capability that has, prior to the present invention, been associated with the presence of such a wire.

Because of the offset positioning of the balloon, and because of the balloon's proximity to the guidewire receiving tube and guidewire, the dilation catheter of the invention has an improved ability to open stenoses. This is because the proximity, of the wire, and the ability of the balloon to contact and bear against that tube and wire, provide the balloon with a firm foundation from which to advance against a stenosis with increased leverage and force. Advantageously, the balloon is specially shaped so that it can bear against the tube and wire without deforming in a way that closes the above-mentioned perfusion channels.

The asymmetrical configuration resulting from the offset positioning of the balloon, also allows the catheter to be expanded into contact with a stenosis with at least two different orientations. In a first orientation, which may be described as a balloon—forward orientation, the relatively flexible outer surface of the balloon is forced against the stenosis while the guidewire receiving tube and guidewire provide leverage and support.

In a second orientation, which may be described as a tube-forward orientation, the relatively inflexible outer surface of the guidewire reinforced tube is forced against the stenoses while the balloon acts as a cushioning and force distributing foundation. In accordance with the invention, either of these orientations (or first one orientation and then the other), and all of the various intermediate orientations, may be established successively as necessary to give the best result for particular stenoses by merely rotating the catheter by appropriate amounts between inflations.

In accordance with an important secondary feature of the present invention, both the balloon and the guide wire receiving tube are secured in abutting relationship to respective parts of the distal end region of the catheter shaft. More particularly, in the preferred embodiment, the proximal end of the balloon is secured in abutting or end-to-end relationship with the part of the distal end of the catheter shaft which surrounds the inflation lumen thereof, and the proximal end of the tube is secured in at least partially abutting relationship to the part of the distal end of the catheter shaft that surrounds the stiffening lumen thereof. One advantage of joining the catheter shaft, balloon and guidewire tube in this way is that it causes the dilation catheter to have a surface which is relatively smooth and featureless, i.e., free of surface irregularities such as radial steps, and which therefore has a reduced tendency to snag on irregularities in the walls of a patient's blood vessels. Another advantage is that it allows the maximum radial or transverse dimension of the catheter to be smaller than would otherwise be the case and therefore usable with smaller blood vessels.

DESCRIPTION OF THE DRAWINGS

Other objects and advantages of the present invention will be apparent from the following description and drawings, in which:

FIG. 1 is an enlarged cross-sectional view of the end section of the preferred embodiment of a dilation catheter constructed in accordance with the present invention, shown as it looks when it is inflated in an unconfined environment;

FIG. 1A is a fragmentary cross-sectional view of an alternative embodiment of the dilation catheter of the invention;

FIG. 2 is a cross-sectional view taken along section 2—2 of the catheter of FIG. 1;

FIG. 3 is a cross-sectional view taken along section 3—3 of the catheter of FIG. 1;

FIG. 4 is a cross-sectional view taken along section 4—4 of the catheter of FIG. 1;

FIG. 5 is a end view of the catheter of FIG. 1, shown with the balloon in its deflated state;

FIG. 6 is a side view of the dilation catheter of FIG. 1, shown as it looks when it is inflated in a confined environment;

DESCRIPTION OF THE PREFERRED EMBODIMENTS

Figure 7:
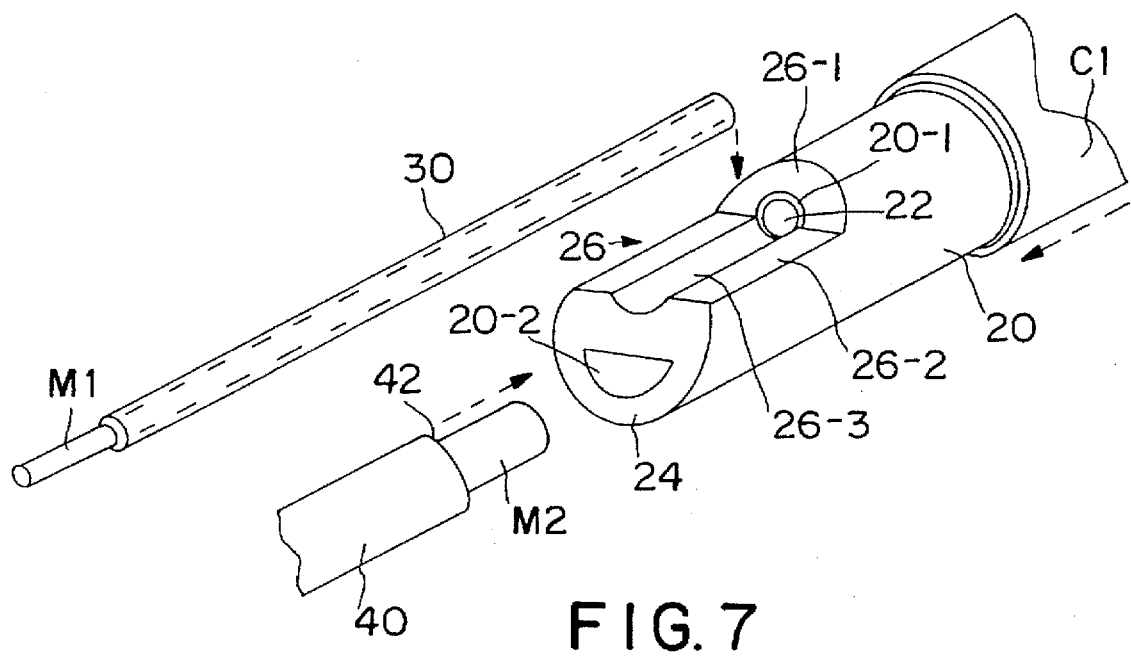
FIG. 7 is a enlarged fragmentary exploded view of the catheter of FIG. 1, showing the mandrels and sleeve used in bonding the proximal sections end of the balloon and the guidewire tube to the distal end of the catheter shaft.

Referring to FIG. 1 there is shown an enlarged cross-sectional view of the distal portion of the preferred embodiment of a dilation catheter 10 which has been constructed in accordance with the present invention. The remainder of catheter 10, which is not shown, has a size and shape that is that same as that shown at section 2—2 of FIG. 1 and comprises an elongated extension thereof. Also not shown is the guiding catheter which surrounds catheter 10 and which serves as a protective sheath through which catheter 10 may be inserted and withdrawn from the cardiovascular system of a patient. In use, the portion of the dilation catheter shown in FIG. 1 projects out of the distal end of the guiding catheter into the region of the stenosis to be dilated. Thus, the portion of the dilation catheter shown in FIG. 1 will be understood to be only the active, end portion of a much longer catheter apparatus.

In the embodiment shown in FIG. 1 catheter 10 includes a catheter shaft 20 which preferably has two lumens and which is composed of a suitable thermoplastic polymeric material, such as polyethylene, nylon or polyethylene tetrafluoride (PET). A first of these lumens 20-1 has a generally circular cross-section, and encloses a wire 22 which imparts longitudinal and torsional stiffness to the catheter, thereby facilitating the insertion and maneuvering thereof. A second of these lumens 20-2 has a generally semi-circular cross section (except at distal end 24 thereof) and serves as an inflation lumen.

Dilation catheter 10 of FIG. 1 also includes a guidewire receiving tube 30 and a dilation balloon 40. In this embodiment, the proximal ends or end sections of the tube 30 and balloon 40 are secured both to respective distal end regions of catheter shaft 20 and to each other, the manner of attachment being such that the proximal end of balloon 40 remains open and in fluid communication with an inflating lumen 20-2. The distal end sections of tube 30 and balloon 40 are attached only to one another, the manner of attachment being such that the distal end of balloon 40 is sealed shut. Thus, fluid can be introduced into or removed from balloon 40 only through lumen 20-2 of catheter shaft 20.

For reasons that will be discussed later in connection with the perfusion capability of the catheter, it is desirable that there not be any attachment between the central or middle portion 30-1 of tube 30 and the central portion 40-1 of balloon 40 and that balloon 40 be given the bowed shape shown in FIG. 1 at the time it is made. One advantage of the absence of such an attachment is that it endows the entire distal end of the catheter with an increased flexibility. Another advantage of the absence of such an attachment is that, together with a bow shaped balloon, it causes a space or gap 40-2 to appear between tube 30 and balloon 40 unless the latter are acted on by an external force that tends to push them toward one another. In FIG. 1 the dilation catheter is shown as it looks when balloon 40 is in its inflated state but is not subjected to such an external force. In FIG. 6 the dilation catheter is shown as it looks when balloon 40 is inflated but is subjected to such an external force. Thus, FIG. 1 may be thought of as showing the appearance of the catheter when it is inflated in an unconfined environment such as the open air. While FIG. 6 may be thought of as showing the appearance of the catheter when it is inflated in a confined environment such as the interior of a patient's blood vessel.

Balloon 40 is preferably preformed in the shape shown in FIG. 1 (except that its distal end section will be open and not flattened and closed as shown in FIG. 1) by inflating a heated length of thermoplastic tubing within an inflation mold having the desired shape. Because, except for the particular shape shown in FIG. 1, this process is well known to those skilled in the art, it will not be described in detail herein. The shape assumed by balloon 40 when it is fully deflated, folded and ready for insertion into a patient, is shown in FIG. 5.

Referring to the right half of the dilation catheter of FIG. 1, it will be seen that the proximal end 42 of balloon 40 is attached in abutting relationship to a first distal end region 24 of shaft 20, and proximal end section 32 of guidewire receiving tube 30 is attached in partly abutting and partly overlapping relationship to a second distal end region 26 of shaft 20. The latter region, which is formed by cutting away part of the upper portion of the distal end section of catheter shaft 20, forms a step (most clearly shown in FIGS. 3 and 7) having a transverse or radial section 26-1 and a longitudinal section 26-2 with a central trough 26-3, the latter being an exposed section of lumen 20-1. Because this step greatly increases the area of contact between the end section of tube 30 and shaft 20, it greatly increases the structural integrity of the bond therebetween. This increase is particularly important because part of the proximal end of tube 30 will be cut away to form an exit port 34 through which a guidewire (represented by dotted line 50 in FIG. 1) will be passed each time the catheter is used in a rapid exchange operation.

The positioning of tube 30 and balloon 40 in abutting, or at least partly abutting, relationship to shaft 20 has a number of advantages. One of these is that this positioning makes the transverse dimension of the dilation catheter, smaller than would otherwise be the case. Having a small transverse dimension is critically important to the use of the catheter since the catheter is of benefit only if it is small enough to fit into the blood vessel in which the stenosis is located and then through the stenosis itself.

Another advantage of positioning tube 30 and balloon 40 in abutting relationship to catheter shaft 20 is that this positioning brings these elements substantially into axial alignment or registry with catheter lumens 20-1 and 20-2, respectively. In the case of balloon 40, the axial alignment is between the proximal end section 42 of the balloon and inflation lumen 20-2. As a result of a thermal bonding step which will be discussed more fully in connection with FIG. 7, this alignment is highly accurate and facilitates a balloon-shaft joint which is substantially free of transverse steps that can cause the dilation catheter to snag during use.

In the case of tube 30, the axial alignment is between the interior lumen of tube 30 and stiffening lumen 20-1 of shaft 20. In the preferred embodiment this alignment results from the fact that the diameter of tube 30 is selected to approximate that of trough 26-3, within which it is positioned when the tube and shaft are bonded together. The advantage of such an alignment is that it assures that, when guidewire 50 is threaded through the lumen of tube 30 via proximal exit port 34 thereof, it is approximately collinear with stiffening wire 22 of shaft 20. This collinearity, together with the proximity of exit port 34 to the distal end of wire 22, assures that catheter 20 has stiffness properties which closely approximate those of dilation catheters which have guidewires that run the full length thereof. Since catheters of the latter type do not have a rapid exchange capability, it will be seen that a catheter constructed in accordance with the invention has both the advantageous properties of non-rapid exchange catheters and the advantageous properties of rapid exchange catheters.

Although the above-described abutting relationships are preferred, the dilation catheter of the invention may also be constructed with the balloon connected in overlapping relationship to catheter shaft 20, as shown in FIG. 1A. More particularly, the proximal end 42 may be fit over and around the distal end 24 of shaft 20, and the proximal end of tube 30 may be draped thereover into contact with the upper surface of catheter 20. Because the use of the catheter structure shown in FIG. 1A requires that the distal end of shaft 20 be shaped in advance to fit into the proximal end of balloon 40, it is more difficult to produce than the catheter shown in FIG. 1. As a result, the catheter embodiment shown in FIG. 1A is not the preferred embodiment of the invention.

In accordance with an important feature of the present invention, the dilation catheter is designed to exhibit a perfusion capability. As will be explained more fully presently, this perfusion capability results, in part, from the fact that balloon 40 is positioned to one side of guidewire receiving tube 30 (i.e., is disposed in an unsymmetrical or offset position) and, in part from the fact that balloon 40 and guidewire receiving tube 30 have different sizes and therefore different curvatures. Together these features assure that channels or grooves appear on both sides of the boundary between tube 30 and balloon 40. Provided only that these channels are large enough, they are able to conduct past the catheter a flow of blood which is great enough to prevent a patient from being exposed to a risk of injury while an angioplasty procedure is being performed.

Referring to FIG. 4 these open channels occupy the regions adjacent to the two edges B1 and B2 of the boundary between tube 30 and balloon 40, and span the full length of central section 40-1 of balloon 40. Because of balloon 40's flexibility, it has a natural tendency to move into and close off these channels, particularly when inflated within the confined space of a blood vessel. This tendency is opposed, however, by the tendency of the balloon to eliminate any externally imposed indentations in the surface thereof. In accordance with the invention, the latter tendency is caused to predominate over the former by forming a concave (or saddle-like) inner surface in the balloon at the time of its manufacture. This concave inner surface serves, in effect, to pre-distort the balloon so that it takes on the desired undistorted shape when it is inflated in the environment in which it is used.

In FIG. 1, which shows the shape of the catheter when balloon 40 is inflated in an unconfined environment, this concavity has the effect of creating open space 40-2. In FIG. 6, which shows the shape of the catheter when balloon 40 is inflated in a confined environment (such as a blood vessel), this concavity has the effect of allowing the inner surface of balloon 40 to come to rest against tube 30 without enveloping or overlapping tube 30 to any significant degree. As a result, when the balloon is inflated within a blood vessel, the catheter assumes the cross-sectional shape shown in FIG. 4 and thereby permits the perfusion of blood past balloon 40. (It will be understood that the term "concave" refers to the shape of the inner surface of the balloon as seen in a longitudinal cross-section taken through the balloon and tube; if the same surface is viewed in a transverse cross section through the balloon and tube, its shape will be convex.)

While the above-described contact between tube 30 and the inner surface of balloon 40 might be eliminated altogether by forming this balloon with a great enough inner surface concavity, the preferred embodiment of the catheter is specifically designed so that this contact does occur. This is because this contact is used in providing one of the important advantages of the invention, namely: the ability of the tube to serve as a relatively stiff foundation or base against which the balloon may bear to gain leverage for its advance against a lesion, thereby better focusing that advance and reducing the pressure necessary to crack the lesion. Without a firm, full length contact between the tube and the balloon the ability to gain such leverage would be greatly reduced or eliminated.

With a firm full length contact between the tube and the balloon, it is possible to take full advantage of the unsymmetrical configuration which the catheter has by virtue of the offset location of its balloon. The catheter may, for example, be used with a "balloon forward" orientation in which the outer surface of the balloon is advanced against a stenosis while the inner surface thereof bears firmly against the relatively stiff body of tube 30 for leverage. Alternatively, the catheter may be used with a "tube forward" orientation in which the outer surface of the tube is advanced against a stenosis while the inner surface thereof is firmly supported by the inner surface of the balloon, which thereby serves as a force distributing base. Such orientations, as well as any of the intermediate orientations, may also be used successively by rotating the catheter through various angles between inflations. Advantageously these rotations are facilitated by the fact that the catheter has a shaft that is relatively stiff as a result of the presence of stiffening wire 22. It will therefore be seen that the catheter of the invention is more effective than previously available catheters and may be used in a greater variety of different ways than previously available catheters.

The manner in which the catheter of the invention is constructed will now be described with reference to FIGS. 7 and 8. Referring first to FIG. 7, there are shown in disassembled form the component parts which are to be brought together to form the proximal portion of the catheter shown in FIG. 1, all parts being labelled with the same numbers used therefor in FIG. 1. Also shown in FIG. 7 are a number of auxiliary components which are used in the making of the catheter and then removed. Among these auxiliary components are metal mandrels M1 and M2, which serve to hold open the lumens of the associated components during the thermal bonding thereof, and a tubular sleeve C1 which serves to clamp the illustrated components together while they are being thermally bonded to one another.

When shaft 20, tube 30 and balloon 40 are ready to be joined, balloon 40, which has previously been preformed into the shape shown in FIG. 1, is pushed against end region 24 of shaft 20 with mandrel M2 extending into lumen 20-2 thereof. This positioning of mandrel M2 assures that the balloon and shaft lumens will take on the same shape during the thermal bonding process. Tube 30, with mandrel M1 in place, is then laid in trough 26-3 and pushed against end surface 26-1 of shaft 20. Mandrel M1 preferably does not at this time extend into lumen 20-1 of shaft 20. This is because it is desirable for the upper portion of the wall of lumen 20-1 to meltingly seal the end of that lumen to the end of stiffening wire 22, as shown in FIGS. 1 and 1A. The joined components are then preferably held in this position by a sleeve C1 which is composed of a material such as silicone rubber or tetrafluorethylene and which is secured thereover in a manner known to those skilled in the art. The joining of these components preferably takes place through an opening in a heat shield S (shown in FIGS. 1 and 8, but not in FIG. 7) which will protect the central section balloon 40 from being deformed by the heat used in the thermal bonding of the end sections thereof.

Once the above-described preparatory steps have been taken, the joined components are thermally bonded by heating them to a temperature dependent on the material used and maintaining them at that temperature for a time long enough for an intimate thermal bond to form therebetween. The formation of this bond preferably involves a degree of plastic flow which rounds off the sharper surface features of the catheter and allows the lumens of the balloon and shaft to take on the same size and shape, as shown in FIG. 1. While this bond does not necessarily obliterate all traces of the previously existing boundaries between the joined components, it has associated with it a considerable degree of cross-linking which renders those boundaries substantially less distinct. The bonded area as a whole may therefore be described as having a substantially integral or monolithic structure.

When the bonding step has been completed and the bonded area has cooled, sleeve C1 is cut away and discarded. After mandrel M1 has been at least partially withdrawn, the exit port 34 for the guidewire may then be formed by cutting away a portion of the proximal end section of tube 30. The area of the cut may, if desired, then be subjected to a final thermal finishing step to assure that the edges of port 34 are smooth enough to facilitate the easy passage of the guidewire therethrough.

Figure 8:
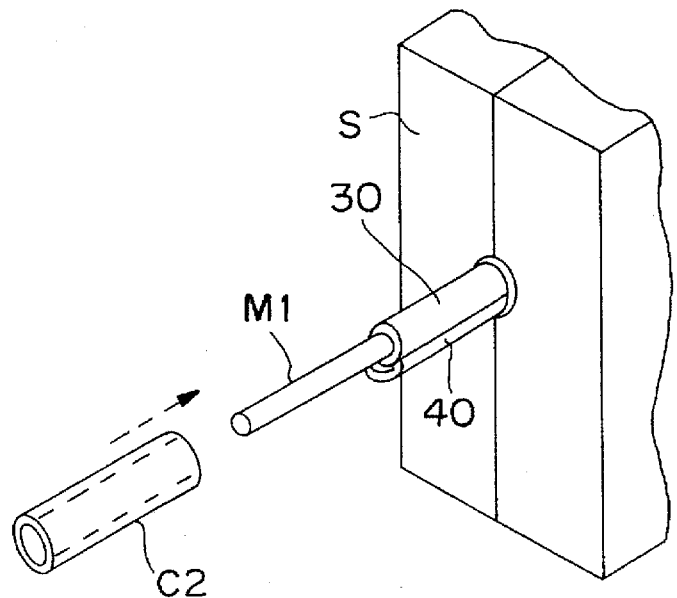
FIG. 8 is an enlarged fragmentary exploded view of the mandrel and sleeve used in bonding the distal end sections of the balloon and guidewire tube.

Referring to FIG. 8, there are shown those parts of tube 30 and balloon 40 which are t0 be bonded together to form the distal portion of the catheter of FIG. 1. These parts include only the distal end sections of tube 30 and balloon 40, the remainder of these components being blocked from view by heat shield S. As shown in FIG. 8, mandrel M1 is present within tube 30 to keep the latter open for the insertion and removal of the guidewire. This distal end section of balloon 40 is flattened against tube 30 to assure that it becomes sealed shut during the bonding step.

In all other aspects the bonding of the distal end sections of tube 30 and balloon 40 is as described in connection with the bonding of the proximal end sections thereof, clamping member C2 being merely a smaller version of previously described clamping member C1. Because of this similarity, the bonding of the components showing in FIG. 8 will not be further described herein.

In the preferred embodiment the tip of the catheter is preferably cut to form a tapered region 44 which facilitates its entry into blood vessels and into the internal opening of a stenosis. If desired, this tapered end may then be subjected to a final thermal finishing step to smooth out any sharp edges produced by the cutting operation.

In view of the foregoing it will be seen that a dilation catheter constructed in accordance with the present invention provides a number of advantages over previously known dilation catheters. One of these is that it combines a rapid exchange capability with a perfusion capability. Another of these is that it provides these capabilities in a catheter which has a relatively small transverse dimension and a surface which is smooth and free of irregularities. Still another of these is that it provides these capabilities in a catheter which is relatively stiff over substantially its entire length and therefore easy to insert and manipulate. Finally, the catheter of the invention includes an offset balloon which, particularly in combination with an associated guidewire, provides a more effective and more flexible way of dilating a stenoses.

While the invention has been described with reference to particular specific embodiments, it will be understood that the true spirit and scope of the invention should be determined only with reference to the appended claims.

What is claimed is:

1. A catheter comprising:

a catheter shaft having a distal end, a proximal end and an inflation lumen;

a guidewire tube defining a guidewire lumen configured to receive a guidewire and having a proximal end and a distal end, the guidewire tube extending forwardly of the distal end of the catheter shaft and defining an exit port for receiving a guidewire; and an inflatable dilation balloon in communication with the inflation lumen of the catheter shaft and including proximal and distal ends, the balloon being attached to the guidewire tube in substantially side-by-side relationship;

wherein the balloon is shaped such that the balloon contacts the guidewire tube when the balloon is inflated within a patient, but bows away from the guidewire tube when the balloon is inflated outside of a patient.

2. A catheter according to claim 1, wherein the catheter shaft includes an auxiliary lumen in which is positioned a stiffening wire extending from the proximal end of the catheter shaft to a location adjacent the exit port in said guidewire tube.

3. A catheter according to claim 2, wherein the stiffening wire is substantially collinear with the guidewire lumen in the guidewire tube.

4. A catheter according to claim 2, wherein the catheter shaft has a circular cross-section enclosing the inflation lumen and the auxiliary lumen.

5. A catheter according to claim 2, wherein the guidewire tube is sealed against a distal end of the stiffening wire located adjacent the exit port in the guidewire tube.

6. A catheter according to claim 1, wherein the balloon is formed as a separate member from the catheter shaft, and the proximal end of the balloon is secured in abutting relationship to the distal end of the catheter shaft.

7. A catheter according to claim 1, wherein the balloon is formed as a separate member from the catheter shaft, and the proximal end of the balloon is secured in overlapping relationship to the distal end of the catheter shaft.

8. A catheter according to claim 1, wherein the balloon is formed as a separate member from the catheter shaft and the proximal end of the balloon is secured to the distal end of the catheter shaft, and the guidewire tube overlaps at least portions of the proximal end of the balloon and the distal end of the catheter shaft.

9. A catheter according to claim 1, wherein the catheter shaft includes a stepped portion which supports the proximal end of the guidewire tube such that a portion of the guidewire tube extends past said stepped portion in a cantilever manner.

10. A catheter according to claim 9, wherein the stepped portion is at the distal end of the catheter shaft and includes a trough and the proximal end of the guidewire tube is disposed in said trough.

11. A catheter according to claim 1, wherein the balloon includes inner and outer surfaces and the inner surface is located nearer the guidewire tube than the outer surface, and the balloon is secured to the guidewire tube with a central section of the inner surface of the balloon unattached to the guidewire tube.

12. A catheter according to claim 1, further comprising a guidewire disposed in said guidewire tube.

13. A catheter comprising:

a catheter shaft defining an inflation lumen;

a guidewire lumen having a proximal end and a distal end, the proximal end including a port for receiving a guidewire;

a balloon including a proximal end, a distal end and an inflatable portion, the inflatable portion of the balloon being in fluid communication with the inflation lumen of said catheter shaft; and a stiffening wire disposed in the catheter shaft, the stiffening wire having proximal and distal ends;

the distal end of the stiffening wire terminating at the port in the guidewire lumen with said stiffening wire being substantially parallel to the guidewire lumen, such that when a guidewire is inserted through said port and into the guidewire lumen the stiffening wire and the guidewire combine to stiffen the catheter over substantially the entire length thereof.

14. A catheter according to claim 13, further comprising a separate guidewire tube which defines said guidewire lumen and is secured to the catheter shaft and balloon.

15. A catheter according to claim 13, further comprising a guidewire disposed in said guidewire lumen.

16. A catheter according to claim 15, wherein the guidewire is substantially collinear with the stiffening wire.

17. A catheter according to claim 15, wherein the catheter shaft includes a stepped portion and the port in the guidewire lumen is located adjacent said stepped portion of the catheter shaft.

18. A catheter according to claim 13, wherein the distal end of the stiffening wire is sealed from the port in the guidewire lumen.

19. A catheter according to claim 13, wherein the balloon includes inner and outer surfaces and the inner surface is located nearer the guidewire lumen than the outer surface, wherein at least a section of the inner surface of the balloon is unattached to the catheter.

* * * * *